(12) United States Patent
Tian et al.

(10) Patent No.: US 11,172,872 B2
(45) Date of Patent: Nov. 16, 2021

(54) FETAL SIZE MONITORING SYSTEM AND METHOD

(71) Applicant: KONINKLIJKE PHILIPS N.V., Eindhoven (NL)

(72) Inventors: Cong Tian, Shanghai (CN); Bin Yin, Shanghai (NL); Lin Li, Shanghai (CN); Mingdong Li, Shanghai (CN); Mian Ding, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 85 days.

(21) Appl. No.: 16/331,160

(22) PCT Filed: Sep. 8, 2017

(86) PCT No.: PCT/EP2017/072610
§ 371 (c)(1),
(2) Date: Mar. 7, 2019

(87) PCT Pub. No.: WO2018/046674
PCT Pub. Date: Mar. 15, 2018

(65) Prior Publication Data
US 2019/0216386 A1 Jul. 18, 2019

(30) Foreign Application Priority Data

Sep. 8, 2016 (WO) ................ PCT/CN2016/098447
Nov. 9, 2016 (EP) ..................................... 16197860

(51) Int. Cl.
*A61B 5/00* (2006.01)
*A61B 7/04* (2006.01)
(Continued)

(52) U.S. Cl.
CPC .......... *A61B 5/4362* (2013.01); *A61B 5/6823* (2013.01); *A61B 5/7235* (2013.01);
(Continued)

(58) Field of Classification Search
CPC ... A61B 5/4362; A61B 5/7235; A61B 5/6823; A61B 7/00; A61B 7/026; A61B 7/04;
(Continued)

(56) References Cited

U.S. PATENT DOCUMENTS 5,140,992 A  8/1992  Zuckermar
5,420,581 A  5/1995  Peters
(Continued)

FOREIGN PATENT DOCUMENTS

CN  103222862 A  7/2013
JP  2014045917  3/2014
(Continued)

OTHER PUBLICATIONS

Hoyer, Dirk, et al. "Indices of fetal development derived from heart rate patterns." Early human development 85.6 (2009): 379-386 (Year: 2009).*

(Continued)

*Primary Examiner* — William J Levicky
*Assistant Examiner* — Alexander M Eisenberg

(57) ABSTRACT

A system for monitoring the fetal size of an expectant mother comprises an acoustic sensor for positioning over the belly of the expectant mother, the acoustic sensor configured to receive an acoustic signal generated by the fetal heartbeat and to generate a sensor output signal. A fetal size is determined from a sensor output signal strength. This system is based on the realization that certain acoustic signals generated by the fetal heart beat are strongly correlated with the fetus size.

19 Claims, 4 Drawing Sheets

(51) Int. Cl.
    *A61B 7/02* (2006.01)
    *A61B 7/00* (2006.01)
    *A61B 8/08* (2006.01)

(52) U.S. Cl.
    CPC ............... *A61B 7/00* (2013.01); *A61B 7/026* (2013.01); *A61B 7/04* (2013.01); *A61B 8/0866* (2013.01); *A61B 2503/02* (2013.01); *A61B 2562/0204* (2013.01)

(58) Field of Classification Search
    CPC ............ A61B 8/0866; A61B 2562/024; A61B 2503/02
    See application file for complete search history.

(56) References Cited

U.S. PATENT DOCUMENTS

| | | | | |
|---|---|---|---|---|
| 6,245,025 | B1* | 6/2001 | Torok | A61B 5/02411 600/500 |
| 10,098,572 | B2 | 10/2018 | Schwenk | |
| 2007/0260155 | A1* | 11/2007 | Rapoport | A61B 5/0444 600/528 |
| 2012/0232398 | A1* | 9/2012 | Roham | A61B 5/02411 600/453 |
| 2016/0270674 | A1 | 9/2016 | Oz | |

FOREIGN PATENT DOCUMENTS

| | | | | |
|---|---|---|---|---|
| WO | WO2007130958 | A2 | 11/2007 | |
| WO | WO2015036991 | A1 | 3/2015 | |
| WO | WO2015071897 | A1 | 5/2015 | |
| WO | WO2016040879 | * | 3/2016 | ............ A61B 7/04 |
| WO | WO2016067276 | A1 | 5/2016 | |
| WO | WO2017037704 | A1 | 3/2017 | |

OTHER PUBLICATIONS

Napolitano, R., et al. "Pregnancy dating by fetal crown-rump length: a systematic review of charts." BJOG: An International Journal of Obstetrics & Gynaecology 121.5 (2014): 556-565. (Year: 2014).*
Nagel J. New diagnostic and technical aspects of fetal phonocardiography. Eur J Obstet Gynecol Reprod Biol. Dec. 1986;23(5-6): 295-303. doi: 10.1016/0028-2243(86)90163-2. PMID: 3542622. (Year: 1986).*
Kovács F, Horváth C, Balogh AT, Hosszú G. Fetal phonocardiography—past and future possibilities. Comput Methods Programs Biomed. Oct. 2011; 104(1): 19-25. doi: 10.1016/j.cmpb.2010.10.006. Epub Dec. 1, 20100. PMID: 21146247. (Year: 2011).*
Baskaran, et al: "Fetal Heart Sound Analysis: A Preliminary Evaluation", Med J Malaysia vol. 51 No. 1 Mar. 1996.
PCT International Search Report, International application No. PCT/EP2017/072610, Dec. 14, 2017.
Nahum G.G. et al., "Predicting Fetal Weight. Are Leopold's Maneuvers Still Worth Teaching to Medical Students and House Staff?", The Journal of Reproductive Medicine, 47.4 (2002): 271-278.
Samieinasab M. et al., "Fetal Phonocardiogram Extraction Using Single Channel Blind Source Separation." Electrical Engineering (ICEE), 2015 23rd Iranian Conference on Electrical Engineering (ICEE), IEEE, p. 78-83, 2015.
Kasoev S.G et al., "Heart Sounds as a Result of Acoustic Dipole Radiation of Heart Valves." Acoustical Physics, vol. 51, No. 6, 2005, pp. 680-687.
Hamill N. et al., "Fetal Cardiac Ventricular Volume Cardiac Output, and Ejection Fraction Determined with 4-Dimensional Ultrasound Using Spatiotemporal Image Correlation and Virtual Organ Computer-Aided Analysis." American Journal of Obstetrics and Gynecology 205.1, 76.e1-76.e10 Jul. 2011.
Kovacs F. et al., "A Rule-Based Phonocardiographic Method for Long-Term Fetal Heart Rate Monitoring", IEEE Transactions on Biomedical Engineering, vol. 47, No. 1, p. 124-130, Jan. 2000.

* cited by examiner

FETAL SIZE MONITORING SYSTEM AND METHOD

CROSS-REFERENCE TO RELATED APPLICATIONS

This patent application claims the priority benefit under 35 U.S.C. § 371 of international patent application no. PCT/EP2017/072610, filed Sep. 8, 2017, which claims the benefit of European Patent Application No. EP16197860.6, filed on Nov. 16, 2016 and application No PCT/CN2016/098447 filed Sep. 8, 2016. These applications are hereby incorporated by reference herein in their entirety.

FIELD OF THE INVENTION

This invention relates to a fetal monitoring system and method, in particular for determining the fetal size.

BACKGROUND OF THE INVENTION

During pregnancy, expectant mothers are keen to obtain information about the movement, size and position of the fetus.

Fetal size and movement are of great importance for evaluating fetal health and wellbeing. Besides the clinical indications, information about the fetal movement, position and/or size provide expectant parents with the knowledge of how the fetus is doing, which gives pleasure and reassurance.

Accurate estimation of fetal size and weight has an important role in routine antenatal care and for detection of fetal growth abnormalities. It is also useful information for selection of the delivery mode.

The most common way to determine the fetal size and weight is by means of fetal imaging. Currently, fetal size is most commonly determined by analyzing an ultrasound image. Ultrasound is the most accurate method for fetal size estimation, but it can only be used in clinics by experienced doctors. In addition, the energy of ultrasound used in clinics is a concern. Both clinical and home-use ultrasound devices should follow the general principle of ultrasound exposure named ALARA (as low as reasonably achievable), and according to regulations, the power output of ultrasound systems for the fetus should be limited to 720 mW/cm$^2$. Even though no study has reported adverse effects relating to performing sonograms on the fetus in clinics, the safety of ultrasound devices for home use is a concern.

Tape measurement of fundal height is another commonly used method in practice. Measurements falling within 1 to 3 cm of the expected value are considered normal. A fundal height with a 4 cm difference compared to an expected value is considered abnormal and suggests the need for further investigation. Fundal height is only a rough indicator for fetal size, and it also includes components relating both to the maternal abdominal size and the fetal size so is not a direct measure of the fetus.

Neither of these procedures is applicable at home, since professional healthcare instruments and/or training are required. However, measurement of fetal size at home is desirable as it could be used to help a pregnant woman to understand their babies' growth trend and wellbeing. However, there is no home-use fetal size measurement device available currently.

SUMMARY OF THE INVENTION

There is a need for detecting the fetal size with a low cost, comfortable and easy-to-use system.

The invention is defined by the claims.

According to examples in accordance with an aspect of the invention, there is provided a system for monitoring the fetal size of an expectant mother, comprising:

an acoustic sensor for positioning above the belly of the expectant mother, the acoustic sensor configured to receive an acoustic signal generated by the fetal heartbeat and to generate a sensor output signal; and a processor for processing the sensor output signal, wherein the processor is adapted to determine a fetal size from a sensor output signal strength.

This system is based on the realization that certain acoustic signals generated by the fetal heart beat are strongly correlated with the fetus size. The distribution and pattern of the fetal heart sound pressure on the abdominal surface of a pregnant woman can be detected by an acoustic sensor (such as a microphone) or a sensor array. An extracted frequency component, for example a peak of the sound pressure in a particular frequency range, is particularly strongly correlated to the fetal size, since the fetal cardiac capability is enhanced with an increase of fetal size. In certain frequency ranges the dominant factor is the power of the fetal heart sound source. The correlation between the fetal size and acoustical signals generated by the fetal heart beat is predetermined to derive the fetal size.

The acoustic sensor may be applied over or on the belly of the expectant mother. The sensor is an acoustic to electrical transducer for converting the acoustic incident signal into an electrical sensor output signal. Note that additional signal treatment may also be conducted before the signal processing, such as amplification and noise reduction, for example based on band pass filtering. Such band pass filtering may be performed both in the analog domain before signal processing and in the digital domain as part of the digital signal processing. The sensor output signal strength is for example a signal strength of one component of the sensor output signal, and the term "signal strength" should be understood accordingly.

The sensor output signal may be stored in memory and a data transmission unit may for example be provided for transmitting the sensor output signal to a remote processor or to the memory, in a wired or wireless fashion.

The fetal heart sound, and in particular the first heart sound, is produced at the moment of closure of the heart valves. In a grown up, the duration of the first sound is about 150 ms and the pressure amplitude (in the stethoscope's bell) is about 3 Pa. A change in the force applied to the valve tissues provides a satisfactory explanation for the main acoustic features of the heart sounds. The invention is based on the recognition that fetal heart sound characteristics may be used to indicate changes in the fetal size. Therefore, the invention provides a device and method for estimating fetal size by analyzing the fetal heart sound characteristics.

The acoustic sensor may comprise a passive sound sensor.

This avoids the need for any introduction of electromagnetic or acoustic radiation into the expectant mother and is thus seen as a safe and easy to use system.

The acoustic sensor may comprise an array of sensor elements.

By using an array of sensor elements, a best signal can be captured, so that the system can function fully for different fetus positions.

The processor may be adapted to extract a frequency component or multiple frequency components from the sensor output signal at a frequency or having a frequency range which lies within 0 Hz to 80 Hz, and to derive the sensor output signal strength from the extracted frequency component or components for fetal size determination.

A low pass filter may be used to extract a low pass frequency range. The cut-off (e.g. 80 Hz) reduces noise from the ambient environment, for example from human speech.

By way of example, the frequency component or one of the frequency components may be at a frequency or may have a frequency range which lies within 0 Hz to 80 Hz, such as 0 Hz to 15 Hz, such as 15 to 20 Hz, such as 40 Hz to 70 Hz.

A band pass filter may be used to extract a narrower range of frequency components, so that specific parts of the fetal heart sound spectrum may be used for the purposes of size estimation. The upper frequency limit means that human speech is filtered out. Lower frequency sounds caused by movement of the amniotic fluid may also be filtered out by the lower frequency limit.

The system may be implemented as a hand held sensor.

This provides a compact system. The hand held sensor may be positioned over the fetus to pick up the heart beat sound.

The processor may then be adapted to generate feedback for the user of the system to assist in placement of the hand held sensor. This makes the process of finding the strongest signal easier for the user of the system.

Instead of a hand held system, the system may be implemented as a belly belt.

In this case, an array of sensors is preferred, so that the system may process multiple signals in order to find the strongest signals to be used for subsequent analysis.

In all cases, the processor may be adapted to determine a fetal size by fitting the sensor output signal strength to a regression model.

The regression model may be built using previous trial data. It may also be tailored to the specific user of the system, for example if input is provided to the system for example following a periodic ultrasound scan. The system can be recalibrated using such input information and the regression model may then be updated accordingly.

Examples in accordance with another aspect of the invention provide a method for monitoring the fetal size of an expectant mother, comprising:

receiving an acoustic signal generated by the fetal heartbeat, using an acoustic sensor which is positioned above the belly of the expectant mother thereby generating a sensor output signal; and processing the sensor output signal thereby to determine a fetal size from a sensor output signal strength.

The method may comprise extracting a frequency component or multiple frequency components from the sensor output signal at a frequency or having a frequency range which lies within 0 Hz to 80 Hz, and deriving a corresponding sensor output signal strength.

The extracted frequency component or components may have a frequency or may have a frequency range which lies within 0 Hz to 80 Hz, such as 0 Hz to 15 Hz, such as 15 to 20 Hz, such as 40 Hz to 70 Hz.

The acoustic sensor may be part of a hand held sensor, wherein the method comprises generating feedback to assist in placement of the hand held sensor.

The fetal size may be obtained by fitting the signal output signal strength to a regression model.

The invention may be implemented at least in part in software.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a system for monitoring the fetal size of an expectant mother which comprises an acoustic sensor for positioning above the belly of the expectant mother, the acoustic sensor configured to receive an acoustic signal generated by the fetal heartbeat and to generate a sensor output signal. A fetal size is determined from a sensor output signal strength. This system is based on the realization that certain acoustic signals generated by the fetal heart beat are strongly correlated with the fetus size.

Figure 1:
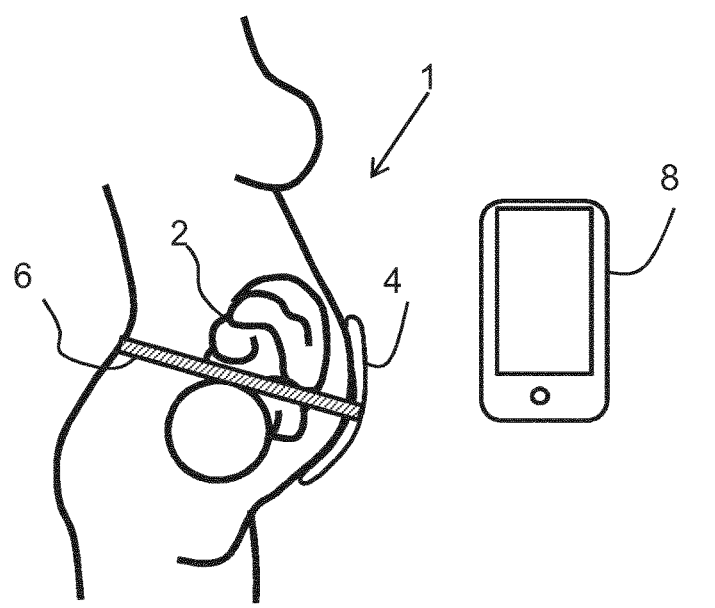
FIG. 1 shows a system for monitoring the size of the fetus of an expectant mother.

FIG. 1 shows a first example of the system being worn by an expectant mother 1. The system is for monitoring the fetus 2. In this first example, an acoustic sensor array 4 is mounted over the belly, held on in this example by a strap 6. It may instead be temporarily adhered in place. The acoustic sensor array provides conversion of an incident acoustic signal into an array of electrical sensor output signals.

A processor is provided for processing the sensor output signals. In the example shown, the processor is provided in a remote device such as a smart phone 8 to which the sensor output signals are transmitted from the sensor array 4 wirelessly. The processor may instead be part of the system, for example a watch-type device. The data communication also may be over a wired connection to the processor rather than wireless. The processing may also be carried out remotely at a central back-end processing location, with communication for example over the internet.

There is a memory for storing the sensor data, and for storing the results of the processing. In the example of FIG. 1, the smart phone 8 implements the memory and processor.

Figure 2:
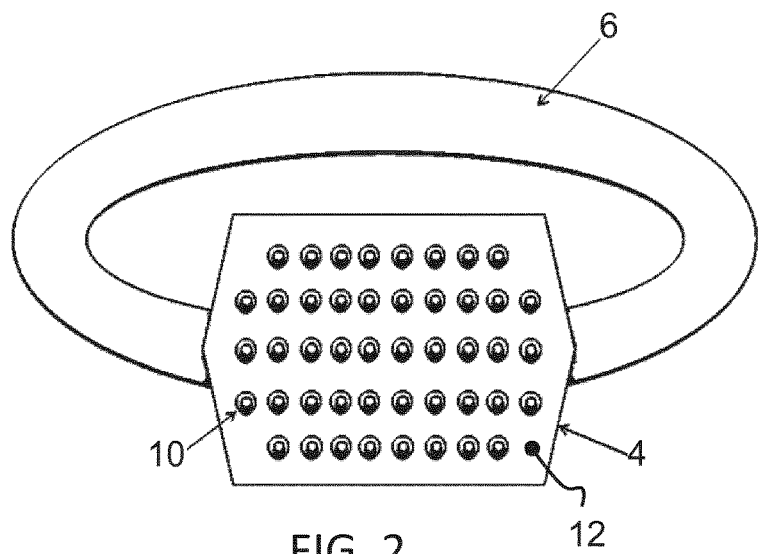
FIG. 2 shows a first example of the sensor in more detail.

FIG. 2 shows the sensor array 4 in more detail. It comprises an array of microphones 10. The microphones are passive sensors, so that there is no need to provide a signal to the abdomen, as would be required for ultrasound sensing.

The microphones essentially measure air pressure, and other pressure sensors may instead be used, for example contact pressure sensors such as piezoelectric sensors or MEMS sensors.

The microphones 10 may be built in to a textile patch 12 that can be worn on the abdomen of the expectant mother, with the help of any suitable fixation mechanism such as the elastic strap 6. Another option is to embed the sensor array into the abdominal portion of maternity clothes, so that the sensor array becomes an integral part of the clothing. In this case, the sensor array 4 needs to be made washable.

The size of the patch 12 is sufficient to cover the abdomen under which the uterus is located. The inter-sensor distance of the microphone array is typically in the range of a few centimeters, for example 1 to 5 cm, and a two dimensional sensor array is provided. The sensors may be evenly distributed over the patch area but this is not essential. They may for example be more densely packed at the locations where the heart signal is usually strongest.

The patch 12 is designed to fit the curvature of the abdomen, and therefore the substrate as well as the wiring among sensors must be, to some degree, stretchable and bendable.

For the patch example, there are preferably at least 5 sensors in the array, and preferably more, for example 10 or more, or even 20 or more, so that there is at least one sensor near an optimum position for detecting the heart beat sound.

The beating heart of the fetus acts as a sound source, creating a sound wave propagating from the fetal heart outwards. This sound wave arrives at the mother's belly, and is picked up by the sensor array.

Figure 3:
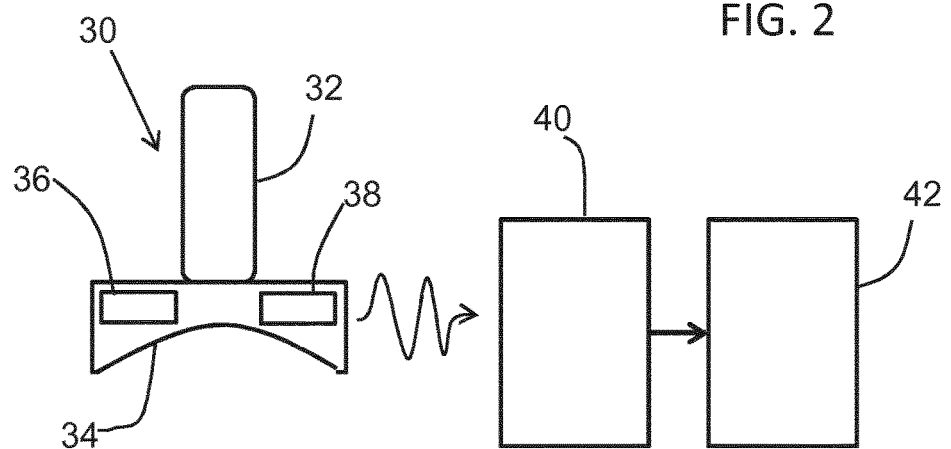
FIG. 3 shows a second example of the sensor in more detail.

FIG. 3 shows a second example of the system. In this example, the system is a hand held acoustic sensor 30 having a handle 32 and a single sensor area 34 such as a vibration film. The hand held part comprises an amplifier 36 and a signal filter 38 such as a band pass filter. The sensor signals are provided to the main control unit 40 which may be remote (as shown) or may be part of the hand held device. The system includes a display and audio system 42, which may again be an integral part of the control unit 40 (as in FIG. 1 where they are both implemented by a mobile device) or the display and audio system may be separate to the rest of the system.

In each case, the acoustic sensor or the acoustic sensors of the array may use an electromagnetic coil or a piezoelectric transducer for acoustic to electrical conversion, for sensing the fetal heart sound propagating through different layers and finally arriving at the maternal abdominal surface.

Figure 4:
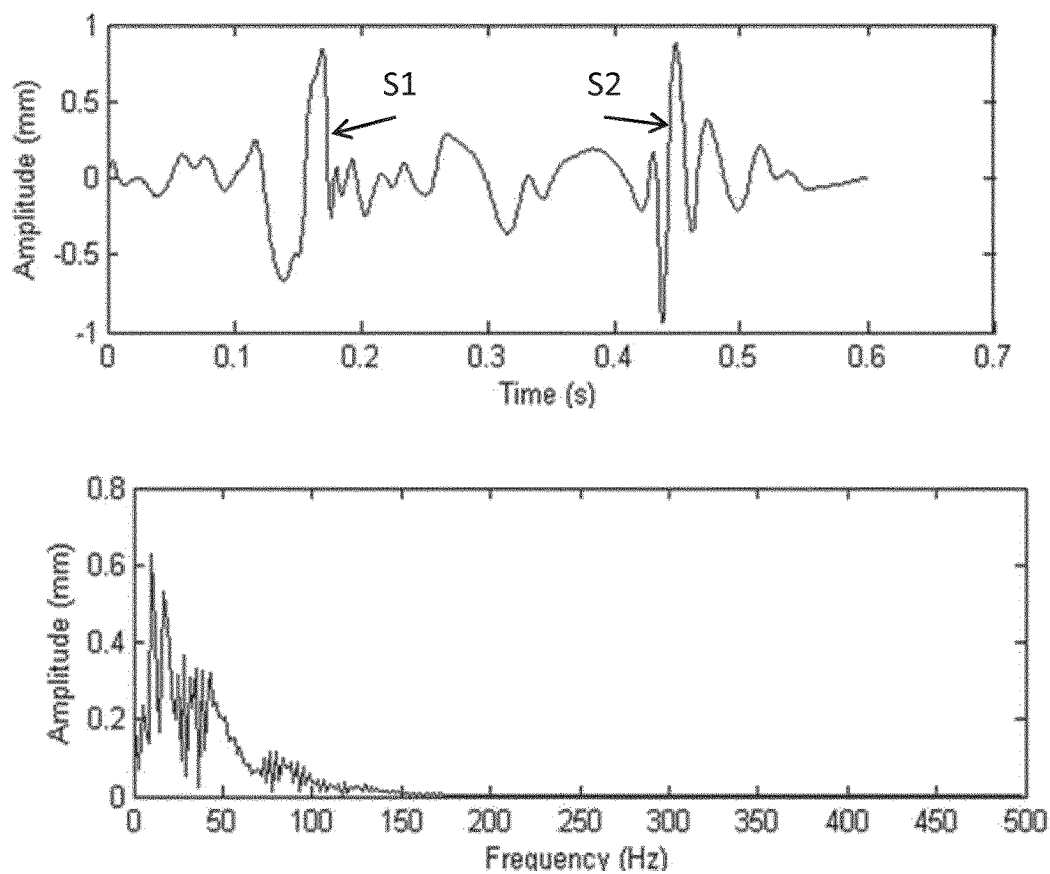
FIG. 4 shows an example of the acoustic signal amplitude over time of a fetal heart sound and the frequency spectrum.

FIG. 4 shows as the top image an example of the acoustic signal amplitude over time of a fetal heart sound, for a single cardiac cycle. The S1 and S2 components are identified. The bottom image shows the frequency spectrum.

One of the features of the fetal heart sound pressure signal of particular interest is the component in a certain frequency range such as 40 to 70 Hz. The fetal cardiac capability increases with an increase of the fetal size, and the effect has been found to be dominant in this frequency range. In particular, the power of the fetal heart sound has most impact in this frequency range.

Other characteristic features of the fetal heart sound may also be identified to provide a stronger correlation with fetal the size or to provide other information of interest. For example a peak pressure at a frequency of around 10 Hz and a peak pressure at a frequency of around 16 Hz are of interest, as will be explained below. In particular, the fetal thorax size and maternal fat and muscle layer thickness can also be identified by using multiple regression models of the peak pressure around 10 Hz, the peak pressure around 16 Hz and the peak pressure in the range 40 Hz to 70 Hz.

In use, the device is applied to the belly region of the expectant mother, preferably at a fixed location above the umbilicus. It may be in contact with the skin, but it may also be spaced from the skin.

For feature extraction from the heart fetal sound spectrum and also for noise reduction, band pass filtering is preferably employed. By way of example, a band pass range of 5 Hz to 80 Hz will filter out most sounds in the human speech range (80 Hz to 880 Hz) as well as low frequency (below 5 Hz) ambient signals and low frequency (below 5 Hz) vibrations which may be caused by vibrations in the amniotic fluid.

Signal amplification provides a stronger signal for processing and also enables the fetal heart sound signal (for example which is lower than 3 Pa) to be amplified so that the sound can be output from a speaker.

In use of the patch or belt system, the system is simply worn, and the processing of the different sensor signal may involve selecting the sensor which has the highest signal strength or highest signal to noise ratio, or selecting a combination of sensor signals. In use of the hand held system, the user holds handle 32 and moves the device around the umbilicus area. The control unit 40 then monitors the sound pressure continuously to find a best position for detection.

Preferably, the most powerful signal, namely having the largest sound pressure, is used for measurement of the heart sound pressure. Feedback is provided by the display and audio system 42 to indicate when the optimum detection position is found. Guidance may also be given to assist the user in moving to the optimum position, for example a series of audible pulses which increase in frequency towards the desired detection area. Guidance may also be provided using the screen.

After the position of the hand held unit has been set, the main control unit monitors the heart beat sound for a time period, and analyzes the sound pressure in the particular spectral range of interest, such as 40 Hz to 70 Hz. This involves extracting frequency components of interest from the large bandwidth signal received. The filtering used may be performed in the analog or digital domain.

More generally, it is low frequency sounds which are of interest, for example a filtered (extracted) acoustic signal of interest may have a frequency range which lies within 0 Hz to 80 Hz. A frequency or a frequency range of interest may thus lie within 0 Hz to 80 Hz, such as 0 Hz to 15 Hz, such as 15 to 20 Hz, such as 40 Hz to 70 Hz. Individual frequencies may be selected within the range or else analysis of a peak with a range or sub-range may be of interest.

The sensor output signal strength (i.e. measured signal intensity) for the particular frequency or the maximum sensor output signal strength across the chosen band of frequencies is then used as the measurement signal. To provide an estimation of fetal size, this measurement signal is applied to an algorithm based on regression analysis. An example of this regression analysis will now be explained.

Figure 5:
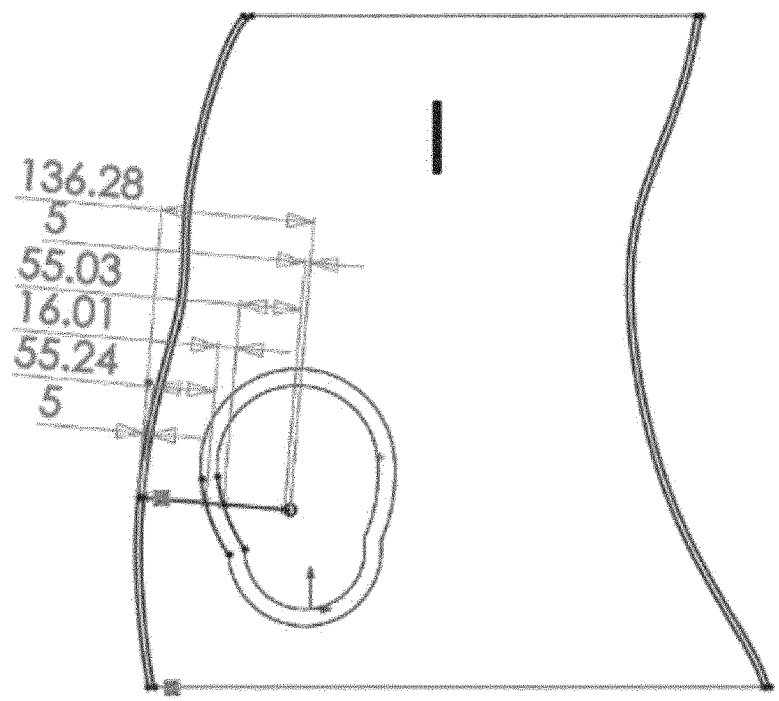
FIG. 5 shows a representation of a typical fetus at a relatively early stage of development.

FIG. 5 shows a representation of a typical fetus at a relatively early stage of development, with a fetal heart circumference of 62.8 mm. It shows a thickness of soft tissue between the fetus and the belly surface of 55.24 mm and a fetal width (between the heart and the fetus surface) of 55.03 mm. These dimensions are all placed in a model which takes account of the density and bulk modulus of different tissue types.

Table 1 below shows the different tissue types with examples of density and bulk modulus values.

TABLE 1

| Component | Density (kg/m3) | Bulk Modulus (GPa) |
| --- | --- | --- |
| Skin | 1120 | 3.75 |
| Maternal supporting tissue | 993 | 3.45 |
| Uterine muscle | 1052 | 9.43 |
| Fetus | 1052 | 3.00 |
| Fetal heart | 1052 | 2.50 |

FIG. 5 shows the skin thickness as 5 mm, the heart dimension (radius) as 5 mm, and the uterine muscle as 16.01 mm.

Using a simulation model to represent the sound propagation, the detected sound spectrum has been modeled. The modeling is for five different fetus sizes.

Table 2 below shows the parameters for the five models.

TABLE 2

| No. | Fetal heart circum' (mm) | Fetal volume (cm$^3$) | Peak 10 Hz (Pa) | Peak 16 Hz (Pa) | Peak 50 Hz (Pa) | Soft tissue thick (mm) | Fetal width (mm) | Dist' (mm) |
|---|---|---|---|---|---|---|---|---|
| I | 62.8 | 2112.718 | 1.085819 | 0.77272 | 0.11 | 55.24 | 55.03 | 136.28 |
| II | 125.6 | 7718.599 | 1.103914 | 0.95929 | 0.25 | 83.87 | 57.24 | 171.35 |
| III | 219.8 | 21669.44 | 1.046359 | 0.93439 | 0.35 | 92.22 | 81.97 | 211.91 |
| IV | 125.6 | 9305.269 | 1.113210 | 0.95422 | 0.23 | 88.14 | 61.20 | 179.58 |
| V | 125.6 | 10294.71 | 1.112994 | 0.95441 | 0.23 | 83.88 | 65.47 | 179.58 |

The model I is that shown in FIG. 5.

Figure 6:
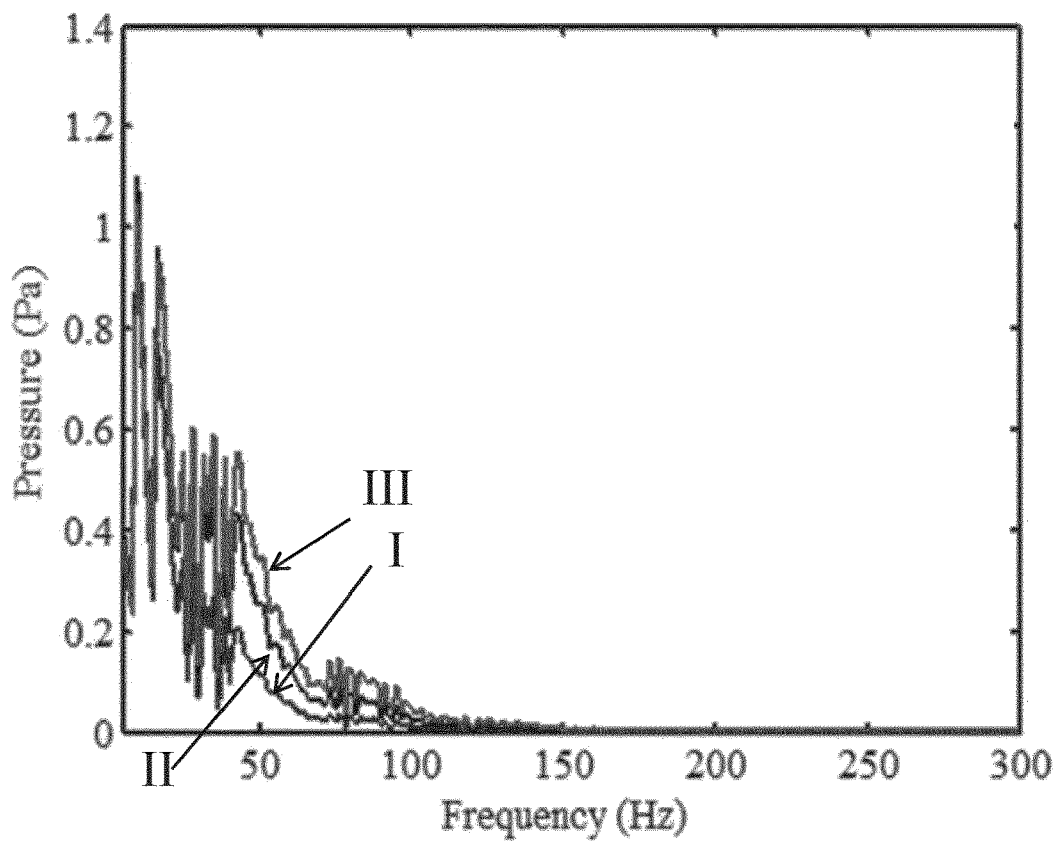
FIG. 6 shows simulation results for the pressure wave created by the fetal heart at different stages of development.

By using the model to apply the same fetal sound pressure per unit area of the surface of the fetal heart (so there is the same power density) the simulation results shown in FIG. 6 were obtained. This shows pressure vs. frequency plots for models I, II and III of Table 2.

It can be seen that in the 50 Hz to 70 Hz band, the fetal heart sound pressure increases with the enlargement of fetal size.

Figure 7:
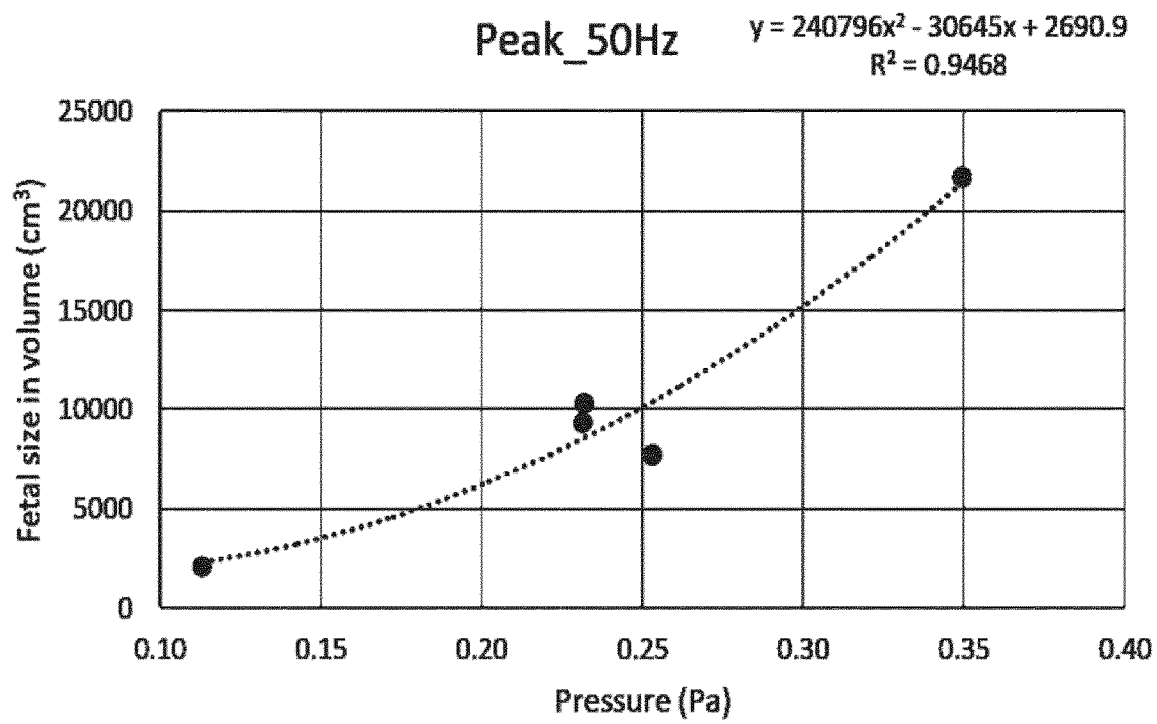
FIG. 7 shows the fetal volume versus the peak pressure at 50 Hz.

This can be seen more clearly in FIG. 7, which shows the fetal size (volume) versus the peak pressure at 50 Hz, for all five models I to V.

From the simulation data, the association between fetal size and fetal heart sound pressure can be derived using a quadratic regression model.

One example of a regression equation which can be used for estimation is:

$$y=444054x^2-122644x+10305 \quad \text{(Eq. 1)}$$

In this example the $R^2$ regression measure is 0.9468.

By using the regression equation, the fetal size (y=fetal volume in this example) can be estimated.

Note that a general regression model may be used if there is no specific information about the expectant mother. However, there is preferably a calibration stage. For example, the system may be used after a first ultrasound scan, and information from that ultrasound scan may be input to the system to adapt the regression model to the particular subject. Further ultrasound scans may be used to increase the accuracy of the regression model. Thus, the model may be tailored to specific subjects.

All relevant information may be shown in the display which may be part of a portable device such as a mobile telephone or tablet, a computer, or may even be projected directly upon the abdomen of the expectant mother. A speaker in any form (e.g. standalone loudspeaker or mobile phone speaker) may be driven to enable the expectant mother to listen to the heart beat sound.

The fetal size may be used to provide an estimate of fetal weight. This may for example enable an expectant mother to monitor her weight gain during pregnancy. Knowledge of the fetal weight can provide a reassurance for pregnant women to manage their own body weight without compromising fetal health and wellbeing. The desire to ensure that weight gain during pregnancy is at healthy levels is one of the main concerns of pregnant women.

Figure 8:
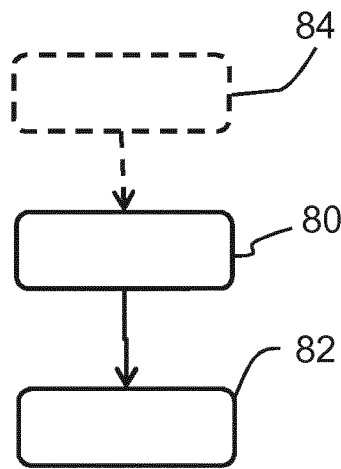
FIG. 8 shows a method for monitoring the fetal size of an expectant mother.

FIG. 8 shows a method for monitoring the fetal size of an expectant mother. The method comprises in step 80 receiving an acoustic signal generated by the fetal heartbeat, from an acoustic sensor which is positioned over the belly of the expectant mother. This generates a sensor output signal.

In step 82 the sensor output signal is processed thereby to determine a fetal size from a sensor output signal strength.

Optionally, there a positioning procedure 84 for a hand held device before the capture of acoustic signals.

The processing 82 involves extracting an acoustic signal from the sensor output signal at a frequency or having a frequency range which lies within 0 Hz to 80 Hz, such as 0 Hz to 15 Hz, such as 15 to 20 Hz, such as 40 Hz to 70 Hz.

The system described above makes use of a controller or processor for processing the sensed data and for performing the data analysis.

Figure 9:
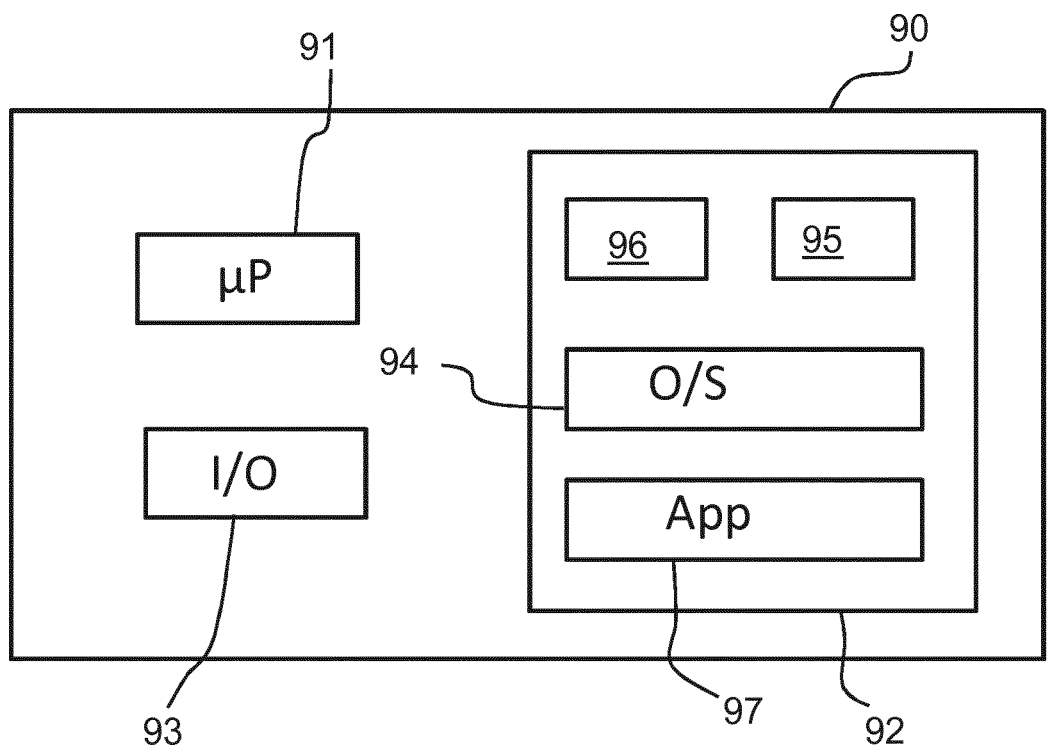
FIG. 9 illustrates an example of a computer 90 for implementing the controller or processor of the system.

FIG. 9 illustrates an example of a computer 90 for implementing the controller or processor described above.

The computer 90 includes, but is not limited to, PCs, workstations, laptops, PDAs, palm devices, servers, storages, and the like. Generally, in terms of hardware architecture, the computer 90 may include one or more processors 91, memory 92, and one or more I/O devices 93 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 91 is a hardware device for executing software that can be stored in the memory 92. The processor 91 can be virtually any custom made or commercially available processor, a central processing unit (CPU), a digital signal processor (DSP), or an auxiliary processor among several processors associated with the computer 90, and the processor 91 may be a semiconductor based microprocessor (in the form of a microchip) or a microprocessor.

The memory 92 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 92 may incorporate electronic, magnetic, optical, and/or other types of storage media. Note that the memory 92 can have a distributed architecture, where various components are situated remote from one another, but can be accessed by the processor 91.

The software in the memory 92 may include one or more separate programs, each of which comprises an ordered listing of executable instructions for implementing logical functions. The software in the memory 92 includes a suitable operating system (O/S) 94, compiler 95, source code 96, and one or more applications 97 in accordance with exemplary embodiments.

The application 97 comprises numerous functional components such as computational units, logic, functional units, processes, operations, virtual entities, and/or modules.

The operating system 94 controls the execution of computer programs, and provides scheduling, input-output control, file and data management, memory management, and communication control and related services.

Application 97 may be a source program, executable program (object code), script, or any other entity comprising a set of instructions to be performed. When a source program, then the program is usually translated via a compiler (such as the compiler 95), assembler, interpreter, or the like, which may or may not be included within the memory 92, so as to operate properly in connection with the operating system 94. Furthermore, the application 97 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 93 may include input devices such as, for example but not limited to, a mouse, keyboard, scanner, microphone, camera, etc. Furthermore, the I/O devices 93 may also include output devices, for example but not limited to a printer, display, etc. Finally, the I/O devices 93 may further include devices that communicate with both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 93 also include components for communicating over various networks, such as the Internet or intranet.

When the computer 90 is in operation, the processor 91 is configured to execute software stored within the memory 92, to communicate data to and from the memory 92, and to generally control operations of the computer 90 pursuant to the software. The application 97 and the operating system 94 are read, in whole or in part, by the processor 91, perhaps buffered within the processor 91, and then executed.

When the application 97 is implemented in software it should be noted that the application 97 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The system and method described above may be used for fetal/pregnancy monitoring products.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for monitoring fetal size of a fetus of an expectant woman, comprising:
   an acoustic sensor positioned above the belly of the expectant woman, the acoustic sensor configured to receive an acoustic signal generated by a fetal heartbeat and to generate a sensor output signal; and
   a processor for:
      extracting at least one frequency component from the sensor output signal at a frequency or having a frequency range;
      deriving a sensor output signal strength based on the at least one extracted frequency component; and
      determining the fetal size from the sensor output signal strength based on a predetermined correlation between the fetal size and the sensor output signal strength.

2. The system as claimed in claim 1, wherein the acoustic sensor comprises a passive sound sensor.

3. The system as claimed in claim 1, wherein the acoustic sensor comprises an array of sensor elements.

4. The system as claimed in claim 1, wherein the frequency range lies within 0 Hz to 80 Hz.

5. The system as claimed in claim 4, wherein the frequency component is at a frequency or has a frequency range which lies within 0 Hz to 15 Hz.

6. The system as claimed in claim 4, wherein the frequency component is at a frequency or has a frequency range which lies within 15 to 20 Hz.

7. The system as claimed in claim 4, wherein the frequency component is at a frequency or has a frequency range which lies within 40 Hz to 70 Hz.

8. The system as claimed in claim 1, further comprising a hand held sensor.

9. The system as claimed in claim 8, wherein the processor further generates feedback for the user of the system to assist in placement of the hand held sensor.

10. The system as claimed in claim 1, further comprising a comprising a belly belt.

11. The system as claimed in claim 1, wherein the processor further determines the fetal size by fitting the sensor output signal strength to a regression model.

12. A method for monitoring fetal size of a fetus of an expectant woman, comprising:
   receiving, at a processor, an acoustic signal generated by the fetal heartbeat, using an acoustic sensor which is positioned above the belly of the expectant woman thereby generating a sensor output signal; and
   extracting at least one frequency component from the sensor output signal at a frequency or having a frequency range;
   deriving a sensor output signal strength based on the at least one extracted frequency component;
   determining, via the processor, the fetal size from the sensor output signal strength based on a predetermined correlation between the fetal size and the sensor output signal strength.

13. The method as claimed in claim 12, wherein the frequency range lies within 0 Hz to 80 Hz.

14. The method as claimed in claim 13, wherein the extracted frequency component is at the frequency or has a frequency range which lies within 0 Hz to 15 Hz.

15. The system as claimed in claim 13, wherein the frequency component is at a frequency or has a frequency range which lies within 15 to 20 Hz.

16. The system as claimed in claim 13, wherein the frequency component is at a frequency or has a frequency range which lies within 40 Hz to 70 Hz.

17. The method as claimed in claim 12, wherein the acoustic sensor is part of a hand held sensor, and wherein the method further comprises generating feedback to assist in placement of the hand held sensor.

18. The method as claimed in claim 12, further comprising determining the fetal size by fitting the sensor output signal strength to a regression model.

19. A non-transitory computer-readable medium that stores therein a computer program product, which, when executed on a processor, causes the processor to:
   process a sensor output signal received from an acoustic signal generated by a fetal heartbeat of a fetus using an acoustic sensor positioned above a belly of an expectant woman;
   extracting at least one frequency component from the sensor output signal at a frequency or having a frequency range;
   deriving a sensor output signal strength based on the at least one extracted frequency component; and
   determine the fetal size from the sensor output signal strength based on a predetermined correlation between fetal size of the fetus and the sensor output signal strength.

\* \* \* \* \*